United States Patent
Tago et al.

(10) Patent No.: US 8,262,987 B2
(45) Date of Patent: Sep. 11, 2012

(54) STERILIZING METHOD AND STERILIZING APPARATUS FOR RETORTED PRODUCTS

(75) Inventors: Yoshifumi Tago, Tokyo (JP); Taizou Takai, Tokyo (JP); Keiko Umegae, Tokyo (JP)

(73) Assignee: Toyo Seikan Kaisha, Ltd., Tokyo (JP)

( * ) Notice: Subject to any disclaimer, the term of this patent is extended or adjusted under 35 U.S.C. 154(b) by 570 days.

(21) Appl. No.: 12/307,977

(22) PCT Filed: Jul. 10, 2007

(86) PCT No.: PCT/JP2007/063717
§ 371 (c)(1),
(2), (4) Date: Jan. 8, 2009

(87) PCT Pub. No.: WO2008/007659
PCT Pub. Date: Jan. 17, 2008

(65) Prior Publication Data
US 2009/0311131 A1    Dec. 17, 2009

(30) Foreign Application Priority Data

Jul. 11, 2006 (JP) ................................. 2006-190138
Jun. 6, 2007 (JP) ................................. 2007-150376

(51) Int. Cl.
| | |
|---|---|
| A61L 2/00 | (2006.01) |
| A61L 2/04 | (2006.01) |
| A61L 2/08 | (2006.01) |
| A61L 9/00 | (2006.01) |
| A61L 11/00 | (2006.01) |
| C23F 11/00 | (2006.01) |

(52) U.S. Cl. ................................. 422/38; 422/1; 422/26

(58) Field of Classification Search ................ 422/1, 21, 422/22, 25, 26, 33, 38; 99/371
See application file for complete search history.

(56) References Cited

U.S. PATENT DOCUMENTS 2,134,817 A * 11/1938 Gerber ............................ 99/367
3,446,636 A *  5/1969 Kraus ............................. 426/405
4,170,421 A * 10/1979 Balding et al. ................. 366/144
(Continued)

FOREIGN PATENT DOCUMENTS

JP          58-2666 B2     1/1983
(Continued)

OTHER PUBLICATIONS

English translation of JP 2001-231521, Aug. 2001.*
(Continued)

*Primary Examiner* — Regina M. Yoo
(74) *Attorney, Agent, or Firm* — Westerman, Hattori, Daniels & Adrian, LLP

(57) ABSTRACT

A sterilizing apparatus for retorted products is provided, which can transfer the retorted products unidirectionally to and from a retort and which can heat and sterilize the retorted products homogeneously for a short time, while sliding a carriage carrying the retorted products reciprocally in the retort. The rotating motions of a rotating drive source (16) disposed on the outside portion of the retort (3) are transmitted through a shaft sealing mechanism (13) to a cam mechanism in the retort, and are converted into reciprocal motions by the cam mechanism and transmitted to the carriage (7) carrying the retorted products (4), so that the retorted products can be heated and sterilized while the carriage (7) being slid forward and backward or rightward and leftward of the retort.

16 Claims, 10 Drawing Sheets

U.S. PATENT DOCUMENTS

| | | | | | |
|---|---|---|---|---|---|
| 4,748,816 | A | * | 6/1988 | Arfert et al. | 62/63 |
| 5,849,246 | A | * | 12/1998 | Hashimoto et al. | 422/26 |
| 5,857,312 | A | * | 1/1999 | Walden | 53/437 |

FOREIGN PATENT DOCUMENTS

| | | | |
|---|---|---|---|
| JP | 2001-231521 A | | 8/2001 |
| WO | WO 2005082173 | * | 9/2005 |

OTHER PUBLICATIONS

International Search Report of PCT/JP2007/063717, date of mailing Oct. 9, 2007.

Notification of Transmittal of Translation of the International Preliminary Report on Patentability (Form PCT/IB/338) of International Application No. PCT/JP2007/063717 mailed Jan. 29, 2009 with Forms PCT/IB/373 and PCT/ISA/237.

* cited by examiner

STERILIZING METHOD AND STERILIZING APPARATUS FOR RETORTED PRODUCTS

TECHNICAL FIELD

The present invention relates to a sterilizing method for retorted products in which a solid product or a highly viscous liquid food and the like is packaged in a heat-resistant packaging bag, and to a sterilizing apparatus for carrying out the sterilizing method.

BACKGROUND

Sterilization processing of retorted products having contents such as a liquid food and the like sealed in a packaging bag made of a heat-resistant resin film and the like is carried out by heating the packaging bag in a retort with steam or hot water. However, in the case of sterilization processing of retorted products having a large or thick packaging bag, or having highly viscous contents or containing solid products, heat transfer inside the retort during heating is poor, thereby requiring a long period of time for the product temperature in the center to reach a set temperature, while conversely causing burning or scorching of the contents as a result of the product temperature rising quickly at portions close to the surface of the bag thereby exposing the contents to a high temperature for an extended period of time.

Therefore, in order to solve these problems, the present applicant proposed a sterilizing method and apparatus for sterilizing retort foods in a retort while sliding to the front and back and to the left and right followed by cooling (see Patent Document 1). As shown in FIG. 12, a sterilizing apparatus for carrying out this sterilizing method has a carriage A4 supported by means of wheels A3 on a support table A2 such as a tray provided within a retort body A1, and trays A6, housing a large number of retort foods A5 arranged in a row, are supported by being stacked in multiple layers on the carriage A4.

The carriage A4 is coupled to a driveshaft A9 of a cranking mechanism A8 driven by a motor A7 through a shaft sealing mechanism A10 provided in the retort body A1, and when the motor A7 is driven and rotated, the driveshaft A9 reciprocates in the lengthwise direction of the retort body A1 in conjunction therewith, and the carriage A4 coupled to the driveshaft A9 slides forward and backward in the lengthwise direction of the retort body A1 within the retort body A1 together with the trays A6.

Patent Document 1: Japanese Patent Publication No. S58-2666

However, in the sterilizing apparatus described in Patent Document 1 above, since the motor and cranking mechanism that drive the carriage are provided in close proximity to one end in the lengthwise direction of the retort body, loading and unloading of trays to and from the retort body can only be carried out from the other end, and unidirectional transfer of retort foods in the manner of loading trays housing unprocessed retort foods from one end of the retort body while unloading trays from the other end following completion of sterilization cannot be carried out, thereby placing limitations on the configuration of the retort food production line. In addition, although the driveshaft of the cranking mechanism is coupled to the carriage inside the retort body through the shaft sealing mechanism provided in the retort body, since the shaft sealing mechanism employs a structure in which the driveshaft is sealed by making sliding contact with the driveshaft reciprocating in the axial direction, this shaft sealing mechanism had problems such as the shaft sealing mechanism for maintaining sealing performance being complex. In addition, since the driveshaft of the cranking mechanism during motor rotation reciprocates forward and backward in the axial direction thereof, it was necessary to provide space for the forward and backward stroke of the driveshaft in close proximity to the retort body.

DISCLOSURE OF THE INVENTION

Therefore, an object of the present invention is to overcome the problems of the prior art as described above by providing a sterilizing method and sterilizing apparatus for retorted products capable of sterilizing efficiently and uniformly without creating differences in temperature within a packaging bag and not allowing the occurrence of portions where adequate sterilization effects are unable to be obtained or portions where the contents end up scorching, facilitates unidirectional transfer of loading and unloading of retorted products to and from a retort, increases the degree of freedom of the configuration of a production line, enables a shaft sealing mechanism to be configured easily, and reduces the space occupied by the sliding portion of a carriage exposed outside the retort.

The sterilizing method for retorted products as claimed in the present invention that achieves the above-mentioned object is a sterilizing method for retorted products, in which carriages on which retorted products are placed are slid within a retort while carrying out heat sterilization processing on the retorted products, wherein the driving force of a drive source installed outside the retort is transmitted to the carriages after being converted to reciprocal motion, and the carriages are slid reciprocally at a preset prescribed cycle in the forward and backward or leftward and rightward directions of the retort.

A rotating drive source using a motor installed outside the retort, or a linear reciprocating drive source using cylinder apparatuses provided in a direction perpendicular to the lengthwise direction of the retort, can be employed for the drive source in the present invention. In the case of employing a rotating drive source, the rotary motion of the rotating drive source is transmitted to the carriages after being converted to reciprocal motion by a cam mechanism, enabling the carriages to slide in the forward and backward or leftward and rightward directions of the retort. In addition, in the case of employing a linear reciprocating drive source, the linear reciprocating drive source is provided independently for each carriage, and each carriage is allowed to reciprocate independently in a horizontal direction perpendicular to the lengthwise direction.

In the present invention, at least one of either the cycle or phase of the reciprocal sliding of the carriages can be varied between the carriages arranged in a row in the lengthwise direction in the retort, and the sliding pattern can be changed in accordance with the products to be sterilized by controlling the sliding frequency of the carriages during retort processing.

In addition, the sterilizing apparatus for retorted products of the present invention for carrying out the sterilizing method described above is a sterilizing apparatus in which carriages on which retorted products are placed are slid within a retort while carrying out heat sterilization processing on the retorted products, and comprises: a plurality of carriages which are arranged in a row in the lengthwise direction in the retort, are provided so as to be able to respectively slide reciprocally in the lengthwise direction or a horizontal direction perpendicular to the lengthwise direction, and hold trays housing retorted products; and a reciprocating drive source that allows the carriages to slide reciprocally within the retort, wherein the reciprocating drive source is installed outside the retort.

In the present invention, the reciprocating drive source can be a rotating drive source using a motor installed outside the retort, a rotating driveshaft driven by the rotating drive source can be allowed to rotatably pass through a retort wall by means of a shaft sealing mechanism, the rotating driveshaft can be driven by a cam mechanism within the retort by being coupled thereto, the rotary motion of the rotating driveshaft can be transmitted to the carriages after being converted to reciprocal motion by the cam mechanism, and the carriages can be allowed to slide in the forward and backward or leftward and rightward directions of the retort. The cam mechanism can be constituted by eccentric cams rotated and driven by the rotating drive source, and cam followers attached to the carriages. In addition, a linear reciprocating drive source, which is provided independently for each carriage and uses a plurality of cylinder mechanisms provided in a direction perpendicular to the lengthwise direction of the retort, can also be used as another reciprocating drive source.

A reciprocating drive source that drives the carriages by varying at least one of either the cycle or phase of the reciprocal sliding between the carriages arranged in a row in the lengthwise direction in the retort, can be employed for either of the reciprocating drive sources. Moreover, in the sterilizing apparatus for retorted products according to the present invention, the reciprocating drive source can be controlled by switching on and off and by varying speed during retort processing, and the sliding pattern can also be changed in accordance with the products to be sterilized by controlling the frequency of the drive source of the carriages during retort processing.

According to the present invention, since a rotating drive mechanism that slides carriages is installed outside a retort, doors can be provided in the front and back of the retort enabling loading and unloading of retorted products to be carried out in a single direction, thereby enabling a high degree of freedom in the configuration of a production line containing a retort sterilization step. As a result, unidirectional transfer can be carried out easily in which unprocessed retorted products are loaded from one end of the retort and unloaded from the other end following completion of sterilization, which together with preventing unsterilized products from entering the packaging step, enables the cycle time of the sterilization processing step to be shortened. In addition, since driving force is transmitted to the carriages by a rotating drive source such as a motor or a linear reciprocating drive source such as a cylinder apparatus installed outside the retort after being converted to reciprocal motion, in comparison with the use of a cranking mechanism, only the motor or cylinder apparatus is required to be installed outside the retort, thereby making it possible to reduce the total installation space of the apparatus while also reducing noise and vibrations generated during apparatus operation. In addition, the use of a cam mechanism or linear drive mechanism makes it possible to increase the degree of freedom when selecting the installation site of the rotating drive mechanism. Since sterilization time can be shortened according to the present invention, in addition to improving productivity, steam, hot water, water and electrical utility costs can be reduced thereby making it possible to decrease running costs. In addition, since the time during which products are exposed to high temperatures is shortened, thermal deterioration of the contents is prevented, thereby improving color and flavor after retorting.

In addition, a plurality of carriages can also be made to slide individually by respective and independent drive sources, and in this case, the inertia of the tray carriages decreases enabling compact and low output power sources to be used for the power sources, thereby making it possible to reduce vibrations generated during operation. Moreover, by varying the cycle and phase of the reciprocal motion between the carriages arranged in a row in the lengthwise direction within the retort, vibrations generated due to sliding of the carriages can be more effectively reduced.

Moreover, the sliding pattern of the carriages can be changed arbitrarily in accordance with the products to be sterilized by controlling the frequency of the drive source of the carriages during retort processing, the sliding pattern can be arbitrarily selected even during sterilization, and by sliding at the maximum frequency when the ambient temperature has reached the sterilization temperature by changing the sliding frequency when raising the ambient temperature, sterilizing or lowering the ambient temperature, for example, product temperature can be controlled, thereby enabling retort processing while always sliding under the optimum conditions in accordance with the type of product to be sterilized in terms of contents, size and the like. According to the apparatus of the present invention, the sliding pattern can be changed easily in accordance with the type of product to be sterilized by selecting the optimum pattern and presetting that pattern in the apparatus for each product to be sterilized. In addition, since sliding of the carriages can be held to the absolute minimum, the service life of the retorting apparatus itself is extended. In addition, since two-dimensional sliding is carried out in combination with sliding in the lengthwise direction of the carriers, agitation effects on the contents in the return path are increased, thereby making it possible to further expect the effect of shortening the sterilization time of highly viscous products and products in large bags for commercial use.

Figure 1:
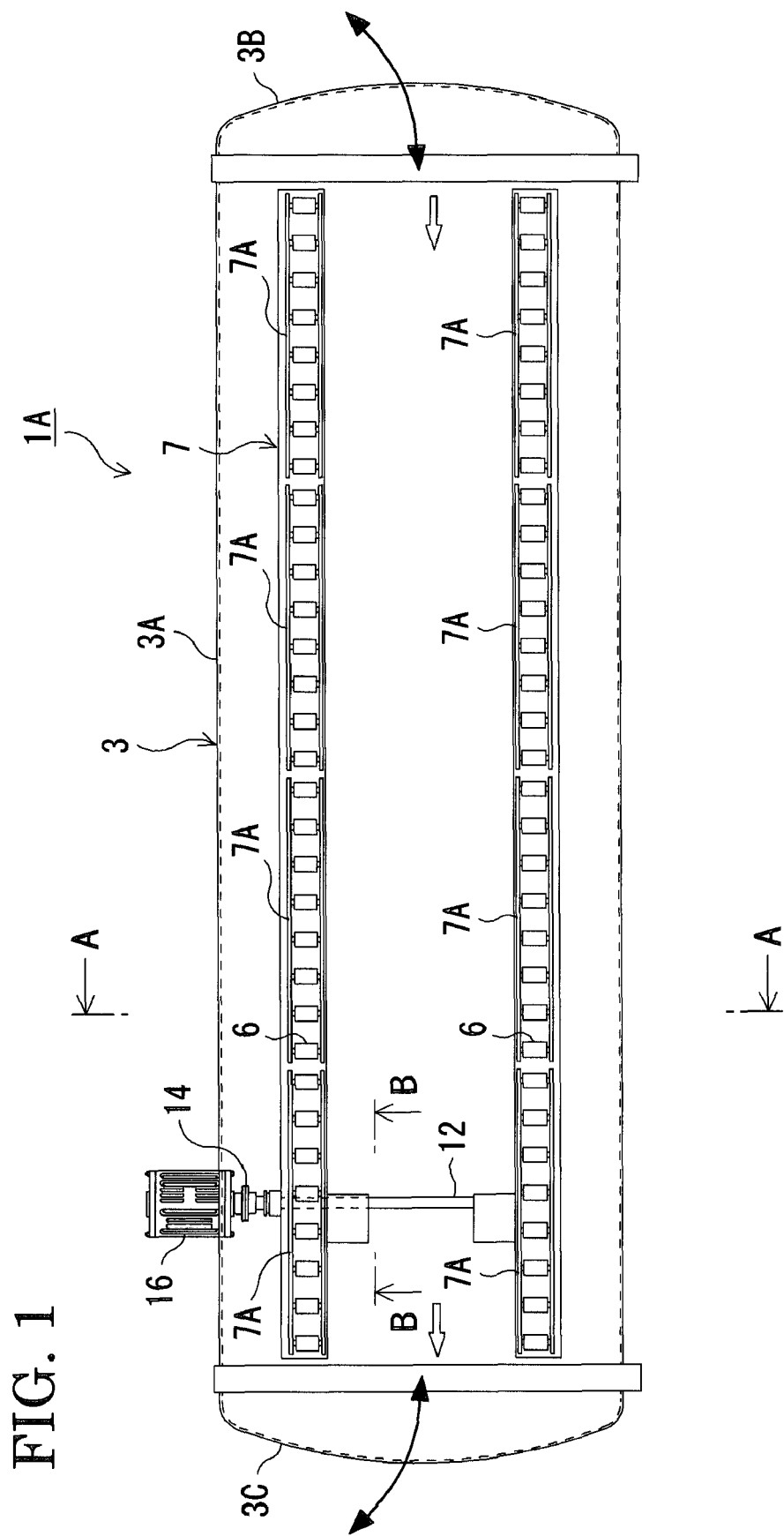
FIG. 1 is an overhead view showing the general structure of a retort sterilizing apparatus used to carry out the retort sterilizing method of the present invention.

EXPLANATIONS OF LETTERS OR NUMERALS 1A,1B,1C Sterilizing apparatus
2 Support leg
3 Retort
3A Retort body
3B,3C Cover
4 Retorted product
5 Tray
6 Tray holding roller
7 Carriage
7A Roller support frame
9,30 Carriage holding roller
10 Cam follower
10A Cam guide surface
11 Eccentric cam
12,12A,12B,12C Rotating driveshaft
13 Shaft sealing mechanism
14 Shaft joint
15 Mounting bracket
16,16A Motor (rotating drive source)
17,18 Gear box
19 Guide rail
20 Traveling guide wheel
21 Relay carriage
22 Dog
23 Roller conveyor
23A Transfer roller
24 Relay roller
25 Relay frame
26 Actuator
27 Stopper
30 Sealing mechanism
36 Coupling rod
37 Support arm
38 Drive source
38A Drive rod

BEST MODE FOR CARRYING OUT THE INVENTION

The following provides an explanation of an embodiment of the present invention based on the drawings.

Figure 2:
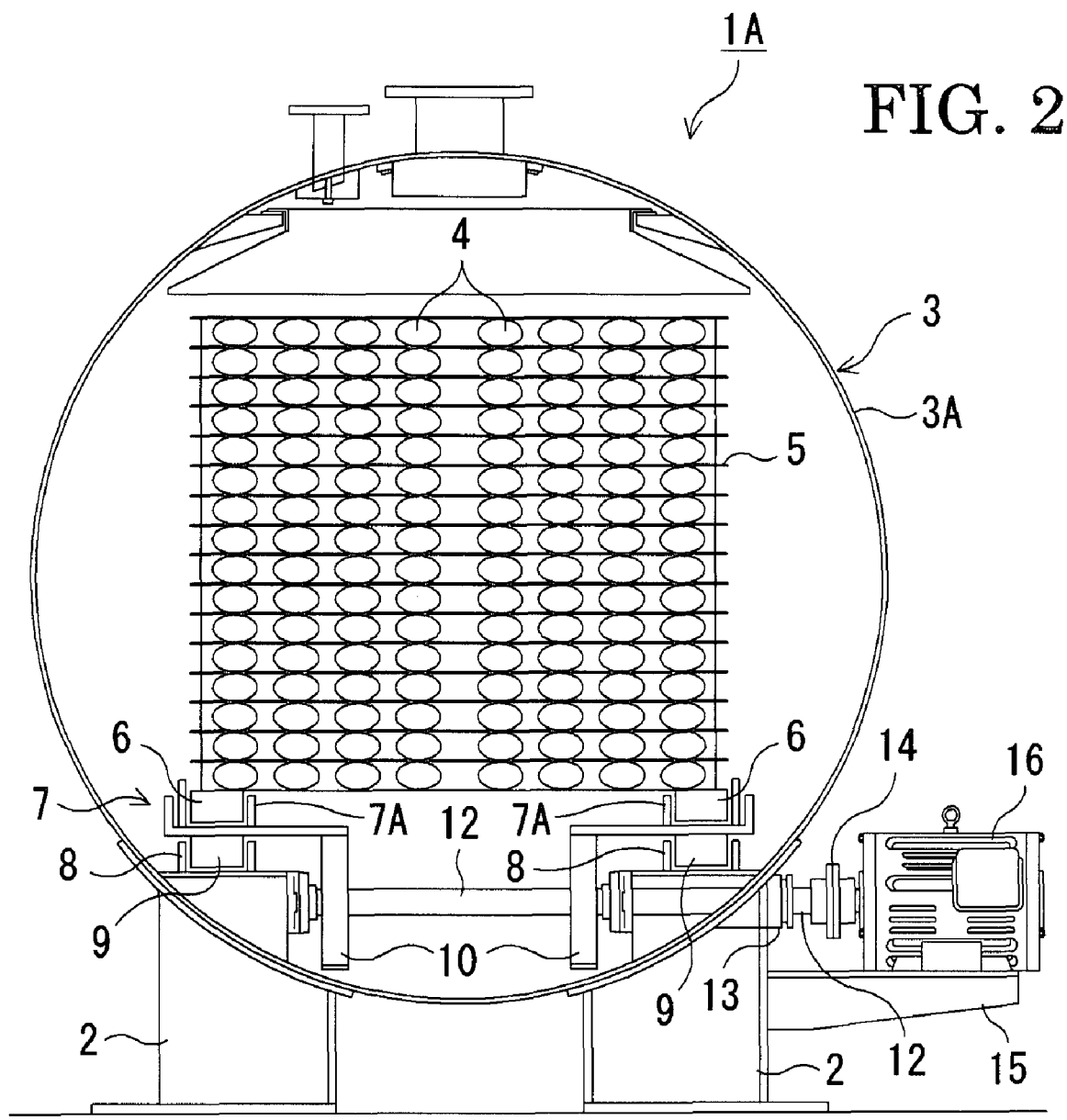
FIG. 2 is a transverse cross-sectional view taken at the location of line A-A of FIG. 1.
Figure 3:
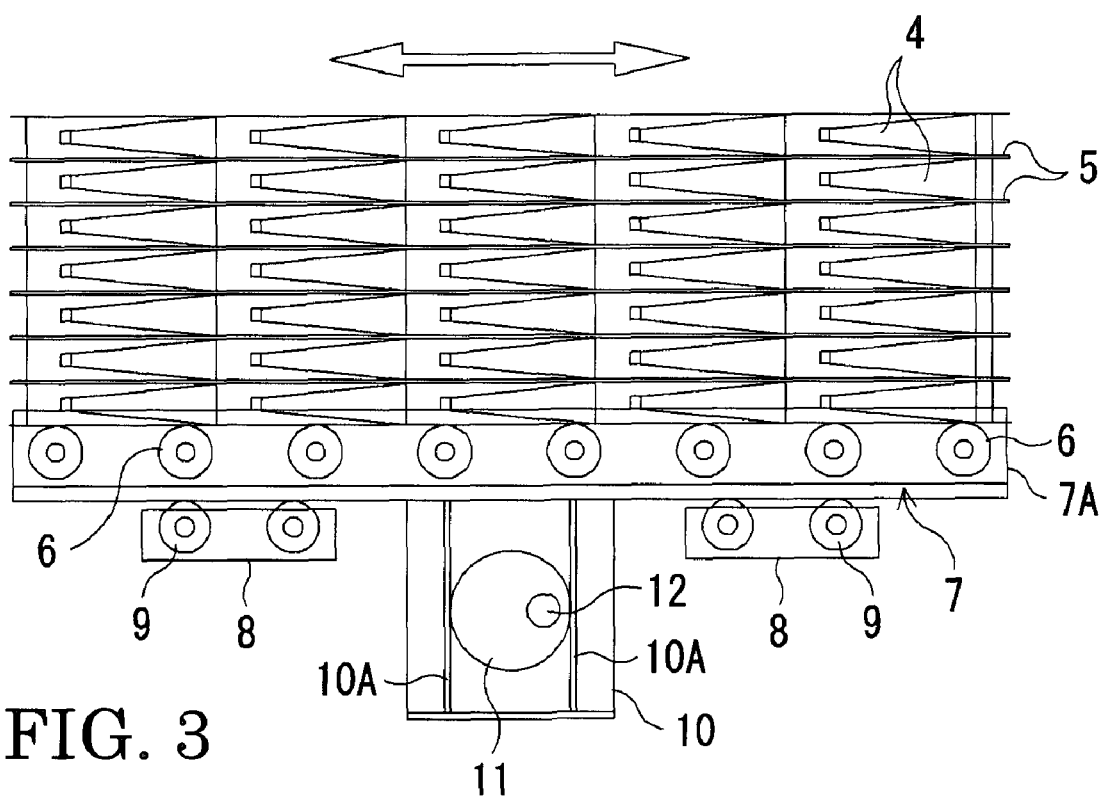
FIG. 3 is a partial cross-sectional view taken at the location of line B-B of FIG. 1.

As shown in FIGS. 1 to 3, a sterilizing apparatus 1A of the present embodiment has a retort 3 held with support legs 2 on a floor surface.

The retort 3 is constituted by a cylindrical retort body 3A and covers 3B and 3C attached to the ends on the front and back in the lengthwise direction thereof. In the present embodiment, a sterilizing apparatus 1 is arranged an intermediate point of a transfer line in a factory not shown with the lengthwise direction of the retort 3 facing in the direction of transfer of the transfer line.

In addition, although not shown in detail, the front and back covers 3B and 3C are each able to be opened and closed, and retorted products not yet sterilized that have been transferred from a previous line with the transfer line are able to be loaded into the retort body 3A by opening the back cover 3B (cover on the upstream side of the direction of transfer, or in other words, the loading side).

In addition, retorted products on which sterilization processing with the sterilizing apparatus 1 has been completed can be unloaded to the downstream side of the transfer line and transferred to the next step by the transfer line by opening the front cover 3C (cover on the downstream side in the direction of transfer, or in other words the unloading side).

Thus, loading of unprocessed retorted products into the retort body 3A of the sterilizing apparatus 1 and unloading of processed retorted products from the retort body 3A can be carried out simultaneously by opening the cover 3B and the cover 3C, and when loading of all unprocessed retorted products into the retort body 3A has been completed, the covers 3B and 3C are closed followed by carrying out sterilization processing of the retorted products by the sterilizing apparatus 1. In addition, in order to prevent contamination by unsterilized products, an interlock control can be provided that only starts loading of unprocessed products after cover 3B has been closed following transfer of sterilized trays.

As shown in FIG. 2, a large number of retorted products 4, which have been loaded into the retort body 3A by a conveyor of the transfer line, are respectively housed in rows on trays 5 stacked in a plurality of layers, and these stacked trays 5 are removably coupled and fixed by a fixing tool not shown so that the stacks thereof do not collapse. Furthermore, these trays 5 are omitted from FIG. 1.

These retorted products 4 have contents sealed in a packaging bag comprising lamination of a heat-resistant synthetic resin and aluminum foil, are inserted one at a time between a large number of dividers provided on the trays 5, and are arranged in rows so as not to shift out of position or fall outside the trays 5 even during vibration of the trays 5.

The lower surfaces in the vicinity of the side edges on both the left and right sides of the lowermost trays 5 stacked in a plurality of layers within the retort body 3A are supported by a plurality of tray holding rollers 6 provided in two rows to the left and right in the lower portion of the retort body 3A. Both ends of these tray holding rollers 6 are rotatably supported with bearings by roller support frames 7A comprising a portion of carriages 7 provided in the lower portion of the retort body 3A, and the trays 5 stacked in a plurality of layers are able to move within the retort body 3A in the lengthwise direction thereof by the rotation of these tray holding rollers 6.

In addition, as shown in FIG. 3, the length of each of these roller support frames 7A is set to be roughly equal to the length of one side of the trays 5 along the lengthwise direction of the retort body 3A, and groups of the trays 5 stacked in a plurality of layers are placed so as to span pairs of roller support frames 7A on the left and right sides. Furthermore, although not shown in the drawing, stopper mechanisms are provided in the vicinity of the ends of each of the roller support frames 7A on the left and right sides in opposition to the lengthwise direction thereof in order to restrict the movement of the groups of trays 5 placed on the tray holding rollers 6, enabling groups of trays 5 to be fixed in position on the left and right pairs of roller support frames 7A during sterilization processing and the like of the retorted products 4.

As shown in FIGS. 2 and 3, the lower surfaces of the roller support frames 7A comprising the carriages 7 are supported on a plurality of rows of carriage holding rollers 9 fixed to the inside and bottom of the retort body 3 and respectively and rotatably supported with bearings by pairs of roller support frames 8 on the left and right sides, and the carriages 7 are able to move freely within a prescribed range in the lengthwise direction of the retort body 3A by allowing these carriage holding rollers 8 to rotate freely.

In addition, as shown in FIG. 2, pairs of left and right cam followers 10 are attached to the carriages 7. Pairs of cam guide surfaces 11A respectively arranged in a row to the front and back in the perpendicular direction as shown in FIG. 3 are formed in these cam followers 10, and eccentric cams 11 are respectively arranged between these cam guide surfaces 10A. These eccentric cams 11 are fixed to a rotating driveshaft 12 rotatably supported with bearings in the lower portion of the retort body 3A in an orientation that transverses to the left and right the lengthwise direction of the retort body 3A. The rotating driveshaft 12 protrudes outside the retort body 3A by passing through the inside of a shaft sealing mechanism 13, and is coupled by a shaft joint 14 to an output shaft of a rotating drive source in the form of a motor 16 fixed on a mounting bracket 15 provided on the side of the support leg 2.

The shaft sealing mechanism 13 employs a structure in which the periphery of the rotating driveshaft 12 is rotatably sealed with a gasket sealing member so that high-temperature and high-pressure steam within the retort body 3A does not escape to the outside during sterilization processing. Furthermore, in the present embodiment, a cam mechanism of the present invention is composed by the cam followers 10 and the eccentric cams 11.

Next, an explanation is provided of the operation of the sterilizing apparatus 1 configured in the manner described above.

Unsterilized retorted products 4 are housed in the trays 5 stacked in a plurality of layer and carried to just in front of the retort 3 by a conveyor of a transfer line not shown where they are temporarily stopped and paused. At this time, the cover 3B of the retort 3 is opened, and a group of the trays 5 stacked in a plurality of layers is transferred onto the tray holding rollers 6 within the retort body 3A from the conveyor of the transfer line. In the present embodiment, although forward movement of the trays 5 stacked in a plurality of layers on the tray holding rollers 6 within the retort body 3A is carried out by being pushed from the outside by allowing the tray holding rollers 6 to rotate freely, each of the tray holding rollers 6 may be synchronously driven collectively for each group of left and right pairs of the roller support frames 7A by a drive source such as a motor not shown.

Furthermore, a means for moving the trays 5 stacked in a plurality of layers within the retort body 3A is not limited to the tray holding rollers 6 driven by a motor and the like, but rather a pushing mechanism can be used that is arranged between the rows of tray holding rollers on both the left and right sides and uses pusher dogs driven with cylinder apparatuses and the like, and the pusher dogs may be made to engage with the lowermost trays 5 so as to push the trays 5 stacked in a plurality of layers forward at a prescribed stroke interval.

Thus, at the point each group of trays 5 stacked in a plurality of layers is pushed in order starting with the first group to the end of each of the roller support frames 7A arranged in series symmetrically on the left and right sides, each lowermost tray 5 is held in position so as not to move forward or backward (lengthwise direction of the retort 3) by a stopper mechanism not shown as a result of being detected by a detection means not shown.

Thus, after all groups of the trays 5 on which are placed retorted products 4 to undergo sterilization processing are loaded into the retort body 3A, the back cover 3B is closed and heat sterilization processing of the retorted products 4 begins within the retort 3. In addition, simultaneous to the start of sterilization processing, the motor 16 provided outside the retort 3 is driven.

When the motor 16 is driven, the rotating driveshaft 12 rotates and the eccentric cams 11 are driven and rotated. As a result, the cam followers 10, having the pair of cam guide surfaces 10A opposing both sides of the outer periphery of the eccentric cams 11, move reciprocally in the forward and backward directions (lengthwise direction) of the retort body 3A accompanying rotation of the eccentric cams 11. Accompanying the reciprocal motion of the cam followers 10, the carriages 7 fixed thereto also slide in the forward and backward directions of the retort body 3A.

Since the movement of the groups of trays 5 stacked in a plurality of layers placed on the carriages 7 is restricted on the carriages 7 by the stopper mechanism described above, the groups of trays 5 also slide together with the carriages 7. Accompanying the sliding motion of the trays 5, the contents of the retorted products 4 housed therein slide within the packaging bags, and as a result thereof, the contents are subjected to agitation effects and temperature unevenness within the packaging bags is reduced, thereby allowing the contents to be sterilized in a short period of time while also making it possible to avoid partially incomplete sterilization and scorching caused by overheating.

Driving of the motor 16 continues even after completion of heat sterilization processing inside the retort 3 to slide the groups of trays 5 while carrying out cooling processing of the retorted products 4. As a result of cooling while sliding the groups of trays 5 in this manner, the time required for cooling can be shortened. Once cooling processing has been completed, covers 3B and 3C provided at the front and back ends of the retort body 3A are opened, and each group of the trays 5 housing the processed retorted products 4 in the retort body 3A are sent out from the front cover 3C onto a conveyor of a transfer line not shown starting with the first group of the trays 5 and transferred to the next step.

At the same time, groups of trays (not shown) housing unprocessed retorted products 4, which have been transferred from the previous step and which are stacked in a plurality of layers and waiting on a conveyor of a transfer line, are sequentially loaded from the side of the back cover 3B into the retort body 3A, and once all of these groups of trays have been loaded into the retort body 3A, the front and back covers 3B and 3C are closed and the previously described processed is repeated.

Furthermore, in the present embodiment, since the front and back covers 3B and 3C of the retort body 3A are opened simultaneously, enabling processed groups of the trays 5 to be unloaded from inside the retort body 3A while groups of unprocessed trays are simultaneously loaded therein, the cycle time of the sterilization processing step can be shortened.

Figure 4:
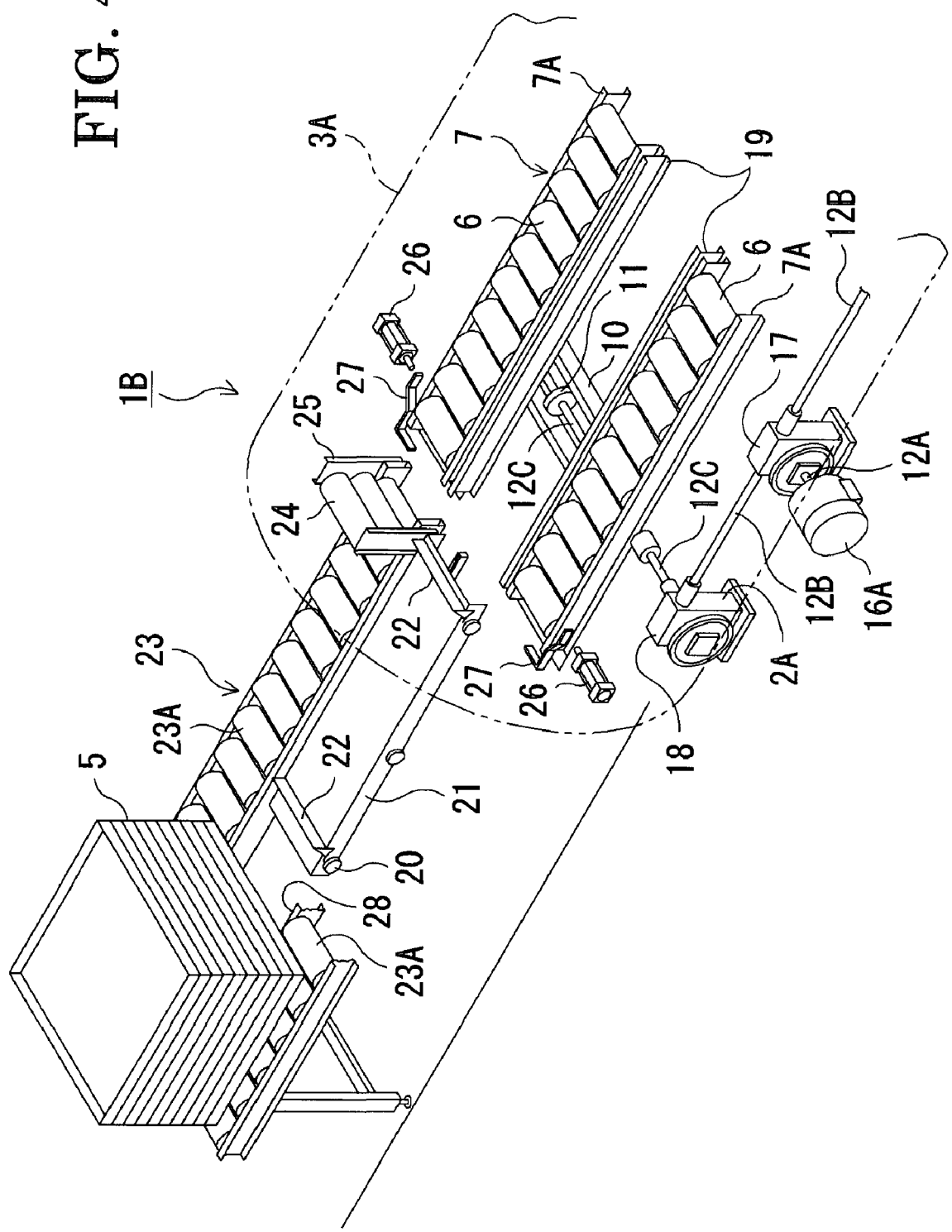
FIG. 4 is a perspective view showing another embodiment of a retort sterilizing apparatus used to carry out the retort sterilizing method of the present invention.

Next, FIG. 4 is a perspective view showing another embodiment of the retorted product sterilizing apparatus as claimed in the present invention. An outline of the contour of the retort body 3A in a sterilizing apparatus 1B is indicated with a virtual line in FIG. 4.

In the sterilizing apparatus 1B, a rotating driveshaft 12A of a motor 16A provided outside the retort body 3A is drivingly coupled to a rotating driveshaft 12B extending in the lengthwise direction of the retort body 3A through a gear box 17 provided on the upper end of a support leg 2A that supports the retort body 3A, and is further drivingly coupled to a rotating driveshaft 12C, the orientation of the rotation axis line thereof being perpendicular to the rotating driveshaft 12B, through a gear box 18 provided on the upper end of an adjacent support leg 2A.

Thus, when the rotating driveshaft 12A of the motor 16A rotates, the rotation thereof is transmitted to the rotating driveshaft 12B and further transmitted to the rotating driveshaft 12C. The eccentric cams 11 are fixed to the rotating driveshaft 12C, and the cam followers 10 are moved reciprocally by the rotation of the eccentric cams 11 as the roller support frames 7A slide.

Furthermore, although not shown in the drawings, the gear box 18 is provided at a plurality of locations along the forward and backward directions (lengthwise direction) of the retort body 3A, and the rotating driveshaft 12C to which the eccentric cam 11 is provided at a plurality of locations corresponding to each of the gear boxes 18.

In addition, the left and right pairs of roller support frames 7A on which the tray holding rollers 6 are arranged are provided in a plurality of groups of rows in the lengthwise direction of the retort body 3A in the same manner as shown in FIG. 1 although not shown in FIG. 4, and each group of the left and right pairs of roller support frames 7A is collectively slid in the forward and backward directions of the retort body 3A by the eccentric cams 11 fixed on the rotating driveshafts 12C provided corresponding thereto.

In the sterilizing apparatus 1B of the present embodiment, free-rolling rollers not having a drive source are used for the tray holding rollers 6, and a relay carriage 21, guided by traveling guide wheels 20 on a pair of left and right guide rails 19 provided on the bottom inside the retort body 3A between the left and right roller support frames 7A, is used for loading and unloading the trays 5 stacked in a plurality of layers. The relay carriage 21 is provided with a pair of dogs 22 that removably retain the front and back ends of the lowermost tray 5 stacked in a plurality of layers by clamping from the forward and backward directions in the vicinity of both ends in the forward and backward directions of the upper surface thereof, and is able to move reciprocally between the inside of the retort body 3A and roller conveyors 23 installed outside the retort body 3A.

The trays 5 stacked in a plurality of layers are housed inside the retort body 3A by being supported in order by left and right transfer rollers 23A provided on the roller conveyors 23, relay rollers 24 and the tray holding rollers 6, and by being pushed by the relay carriage 21. Furthermore, the pair of dogs 22 are comprised to be erected and collapsed by a drive means not shown installed on the relay carriage 21.

The groups of trays 5 housed in the retort body 3A are held in position at a prescribed location with their forward and backward movement relative to the roller support frames 7A being restricted by stoppers 27 driven to advance and retract from both sides above the tray holding rollers 6 by actuators 26 attached at the front and back thereof on the side of the roller support frames 7A.

Although only partially shown in the drawing, the stoppers 27 and the actuators 26, which cause them to advance and retract, are respectively provided on the front and back ends of the pair of left and right roller support frames 7A. In addition, although not shown in detail in the drawing, when the relay carriage 21 is on the side of the roller conveyors 23, the travel thereof is guided by a pair of guide rails having the same structure as the guide rails 19 respectively provided on the insides of the rows of the left and right transfer rollers 23A, and when leaving and entering the retort body 3A, are guided by guides having the same cross-sectional shape as the guide rails 19 respectively formed on a pair of left and right relay frames 25, thereby enabling the relay carriage 21 to transfer to the side of the guide rails 19.

Furthermore, an endless or fluid cylinder apparatus such as a chain or timing belt is used to drive the reciprocating travel of the relay carriage 21, and can be carried out by a drive means equipped with a drive source on the side of the relay carriage 21.

Furthermore, in the present embodiment, since the load to each motor 16A can be dispersed if the gear box 17 driven and coupled to the motor 16A is arranged at a plurality of locations and a common rotating driveshaft 12B is driven by a plurality of the motors 16A, a small motor can be used for the rotating drive source. Moreover, by using carriages having independent groups of roller support frames 7A in which respective groups of left and right pairs slide as a single unit, arranging a plurality of these carriages in series in the retort body 3A, supporting each of the carriages individually while allowing to slide, and causing each carriage to slide in a mutually different phase by varying the phase of the angle of rotation of the eccentric cam 11 that drives each carriage, resonance of the overall sterilizing apparatus can be suppressed, thereby making it possible to reduce the effects of vibrations and noise on the area around the sterilizing apparatus.

In addition, although an eccentric cam mechanism is used as a cam mechanism to slide carriages in the forward and backward directions of a retort in the embodiments explained above, a structure can also be employed in which a cylindrical cam mechanism, for example, is used as a cam mechanism, cam followers are guided in cam grooves formed in the peripheral surfaces of cylindrical cams and the cam followers can be allowed to move reciprocally in the axial direction of the cylindrical cams, and sterilization processing can be carried out while allowing retorted products to slide in the leftward and rightward directions relative to the retort body by supporting the carriages to as to be able to move in the leftward and rightward directions of the retort body.

Figure 5:
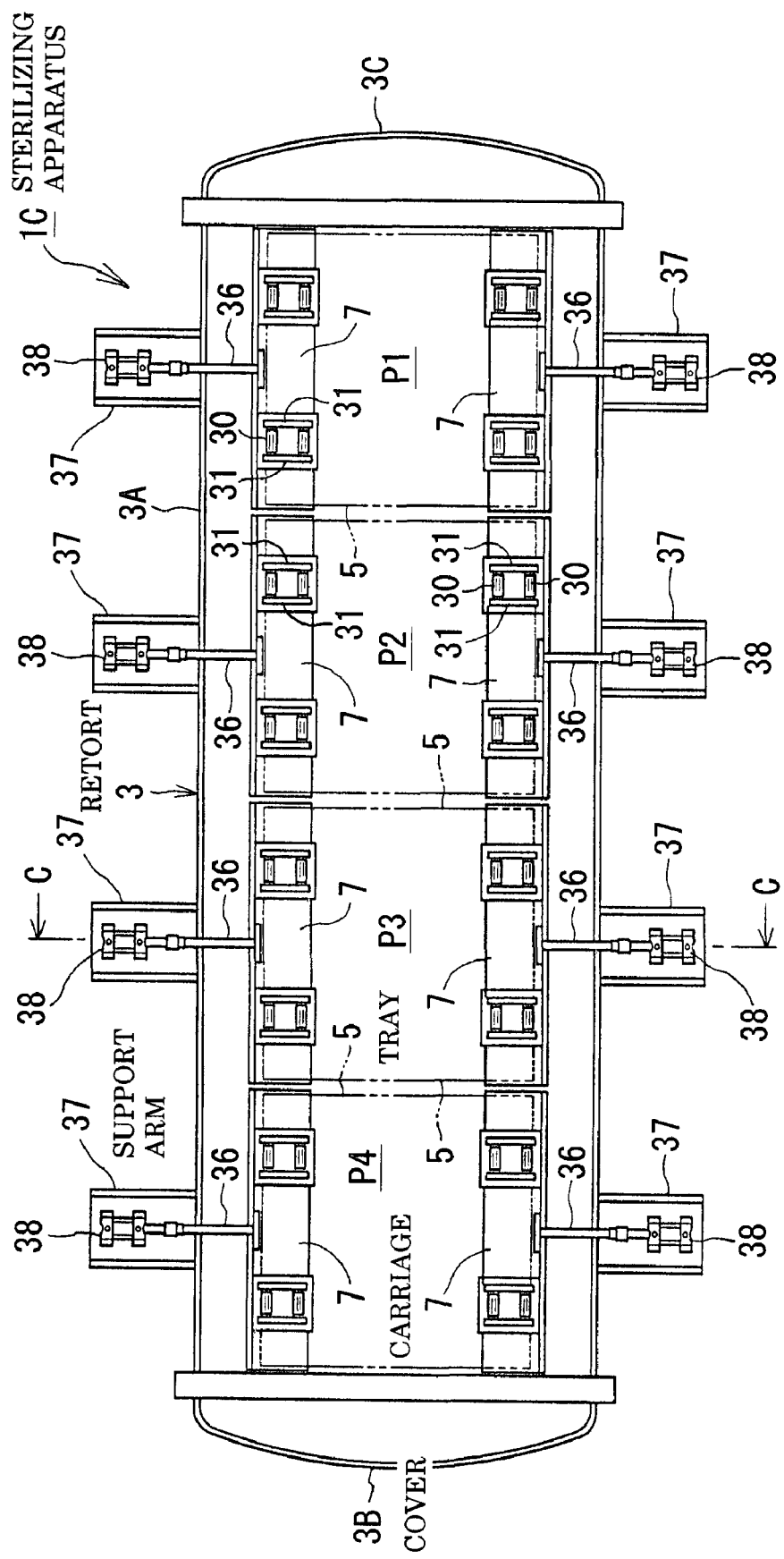
FIG. 5 is an overhead view showing the general structure of a retort sterilizing apparatus used to carry out another retort sterilizing method of the present invention.
Figure 6:
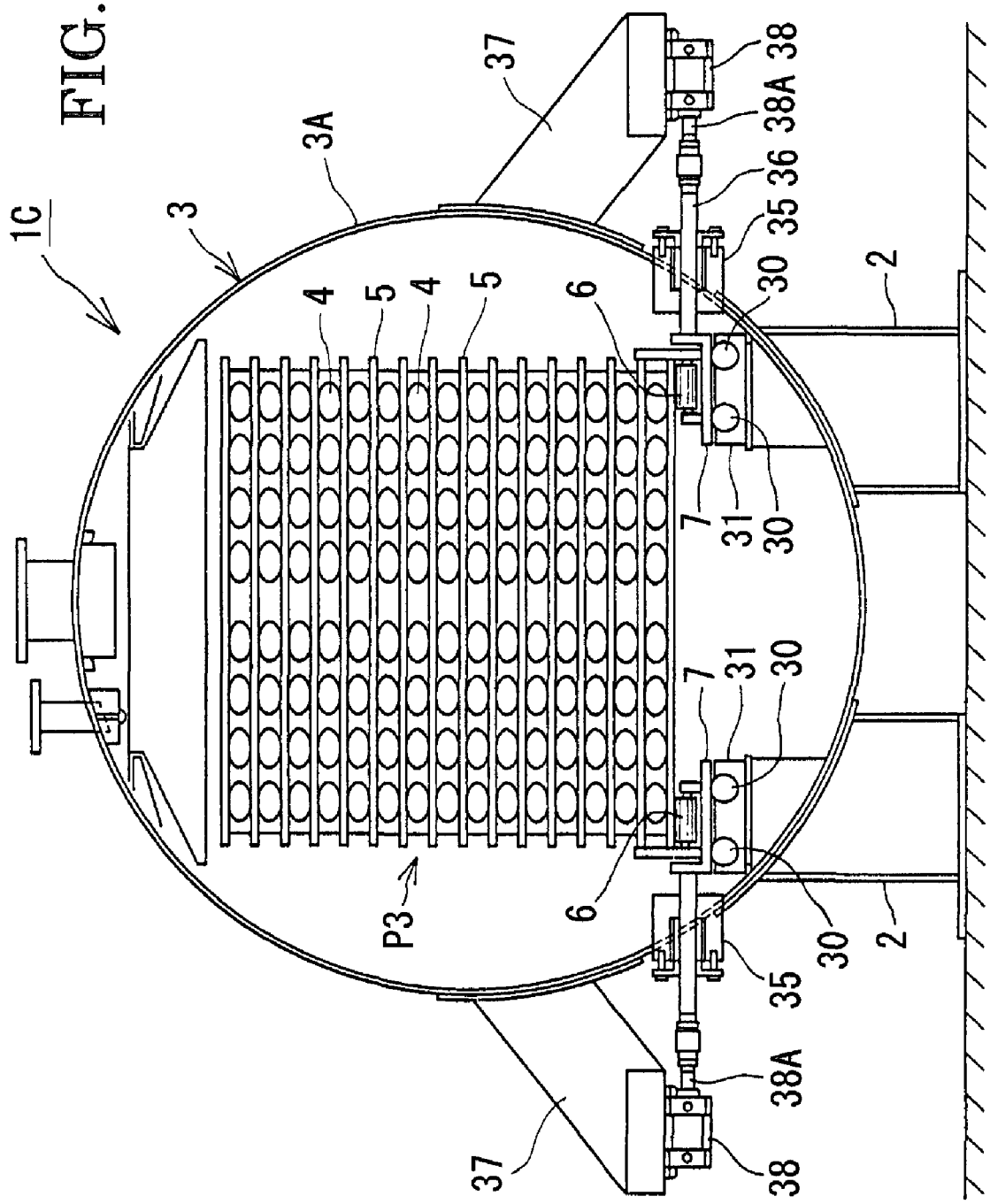
FIG. 6 is a transverse cross-sectional view taken at the location of line C-C of FIG. 5.

FIGS. 5 and 6 show a sterilizing apparatus for retorted products as claimed in another embodiment of the present invention. In the apparatus of this embodiment, drive sources for sliding carriages reciprocally are linear reciprocating drive sources provided independently for each carriage and provided perpendicular to the lengthwise direction of the retort, and the carriages are independently slid in a horizontal direction perpendicular to the lengthwise direction by the linear reciprocating drive sources. The following provides an explanation of those aspects of the present embodiment that differ from those of the previously described embodiments while using the same reference symbols for those portions that are the same for both.

In a sterilizing apparatus 1C for retorted products of the present embodiment, eight carriers 7 within the retort 3 are supported on carriage holding rollers 8 provided in two rows each in the horizontal direction perpendicular to the lengthwise direction of the retort body 3A. These carriage holding rollers 30 are rotatably supported on both ends with bearings by roller holding frames 31 attached to both the left and right sides at the lower portion of the inner periphery of the retort body 3A, and each of the carriages 7 is able to move freely in the horizontal direction perpendicular to the lengthwise direction of the retort body 3A within the retort body 3A by allowing these carriage holding rollers 30 to rotate freely.

In addition, one end of a coupling rod 36, which passes through the peripheral wall of the retort body 3A, is coupled to each carriage 7 through a sealing mechanism 35 that isolates the inside and outside of the retort 3 as shown in FIG. 6. The other end of the coupling rod 36 is coupled to a drive rod 38A provided in a drive source in the form of an air cylinder mechanism 38 attached to a support arm 37 provided protruding from the outer peripheral surface of the retort 3.

As shown in FIG. 5, the air cylinder mechanism 38 is provided in a quantity equal to the number of carriages 7, and in the present embodiment, a total of eight of the air cylinder mechanisms 38 are provided, and each is driven and controlled by a drive control mechanism not shown.

When the driving rods 38A of the air cylinder mechanisms 38 are repeatedly driven to advance and retract at a prescribed cycle and stroke in the horizontal direction perpendicular to the lengthwise direction of the retort 3, the movement of the driving rods 38A is transmitted to the carriages 7 through the coupling rods 36, and the carriages 7 are configured so as to slide in the same direction as the driving rods 38A while being supported by the carriage holding rollers 30.

Here, two groups of carriages 7, respectively supporting the lower surfaces of the lowermost tray 5 of each group of trays 5 stacked in a plurality of layers at both the left and right sides, are driven and controlled in coordination with the air cylinder mechanisms 38 that drive each carriage 7 so that the carriages 7 move at mutually the same amplitude, in the same phase and in synchronization.

Furthermore, two of these carriages 7 may be configured in the form of an integral member by coupling together, and in this case, these integral carriages 7 may be driven using a drive source such as a single air cylinder mechanism. In addition, the drive source for sliding the carriages is not limited to the air cylinder mechanism, but rather a rotating drive source in the manner of a motor, for example, may be used so as to slide the carriages by means of a cranking mechanism.

Although not shown in the drawings, the sterilizing apparatus 1 of the present embodiment may be equipped with drive control apparatuses that allow the cycle and phase of reciprocal motion of the drive rods to be individually set for each of four groups consisting of left and right pairs each of the eight air cylinder mechanisms 38 provided on both sides outside the retort 3.

Next, an explanation is provided of the operation of the sterilizing apparatus 1C configured in the manner described above while focusing on those portions that differ from the previously described embodiments based on the drawings.

After the trays 5 stacked in a plurality of layers in the retort body are positioned by a stopper mechanism not shown and the cover 3B is closed, sterilization processing of the retorted products by heating begins within the retort 3. In addition, together with the start of sterilization processing, each of the air cylinder mechanisms 38 provided outside the retort 3 is collectively driven and each carriage 7 begins to slide in the leftward and rightward directions. As a result, each group P1, P2, P3 and P4 of the trays 5 stacked in a plurality of layers slides reciprocally at a right angle to the lengthwise direction of the retort body.

Accompanying the sliding motion of the trays 5, the contents of the retorted products 4 housed therein slide within the packaging bags. As a result, the temperature of the contents is uniform throughout the entire inside of the packaging bags due to agitation effects, thereby avoiding partially incomplete sterilization and scorching caused by overheating. In addition, the agitation effects on the contents also enable the sterilization time to be shortened.

Furthermore, in the present embodiment, since the sliding cycles and sliding phases of the groups P1, P2, P3 and P4 of the trays 5 can be changed individually, varying these sliding cycles and sliding phases enables resonance of the overall sterilizing apparatus 1C to be suppressed, thereby making it possible to reduce the effects of vibrations and noise on the area around the sterilizing apparatus 1C.

Following completion of sterilization processing, the retorted products 4 continue to undergo cooling processing while sliding the groups P1, P2, P3 and P4 of the trays 5 for a short time thereafter. Cooling the groups P1, P2, P3 and P4 of the trays 5 while sliding in this manner makes it possible to shorten the amount of time required for cooling.

EXAMPLES

Sterilization processing tests were carried out by sliding retorted products at various frequencies in order to confirm the effects of a retort sterilizing method using an apparatus of the present invention. Those results are shown in FIGS. 7 to 10. FIGS. 7 to 10 are graphs showing measurement results when sterilization processing tests were carried out by sliding retorted products at various frequencies, the retorted products used for measurement consisted of 1 kg packages of curry soup, the sterilization temperature within the retort was 120° C., come-up time was 12 minutes, sterilization advances to the next step at a sterilization value in the form of an Fo value of 5, and the sliding stroke of the retorted products was 75 mm.

Here, "come-up time" refers to the amount of time until the ambient temperature inside the retort reaches the sterilization temperature, and a come-up time of 12 minutes means that the amount of time from the start of sterilization to the time the ambient temperature inside the retort reaches 120° C. is 12 minutes. In addition, "advancing to the next step" refers to advancing from the retorted product sterilization step to the cooling step, and here, advancing to the next step at an Fo value of 5 means that the sterilization step advances to the cooling step when the Fo value of the retorted products has reached 5.

Figure 7:
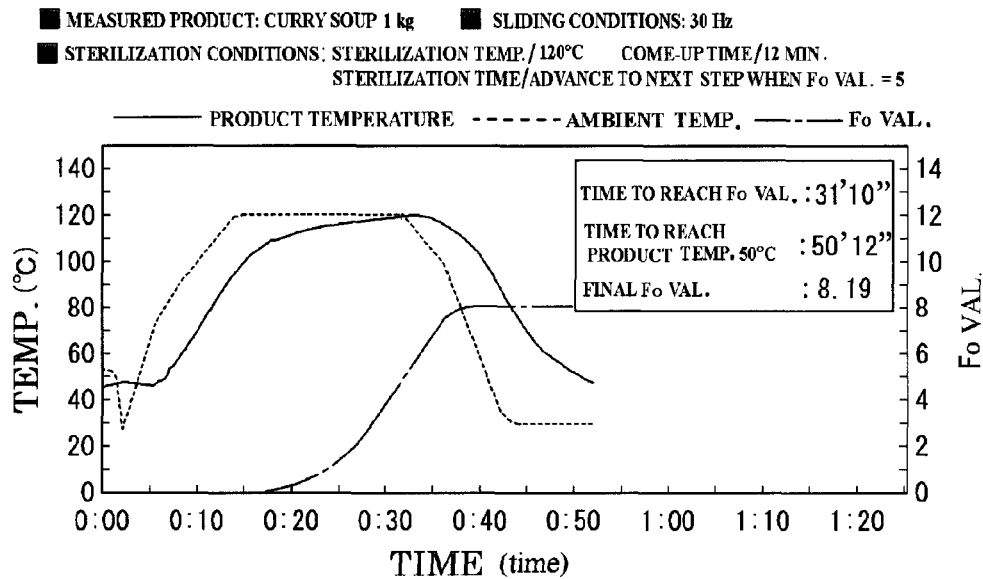
FIG. 7 is a graph showing measurement results in the case of carrying out a sterilization processing test while sliding retorted products at 30 Hz according to the retort sterilizing method of the present invention.

The graph of FIG. 7 shows the results of carrying out sterilization processing while sliding the retorted products at a sliding frequency of 30 Hz, and in this example, the amount of time from the start of sterilization until the Fo value reaches 5 was 31 minutes 10 seconds, the amount of time from the start of sterilization until the product temperature has decreased to 50° C. after entering the cooling step following heating was 50 minutes 12 seconds, and the final Fo value was 8.19.

Figure 8:
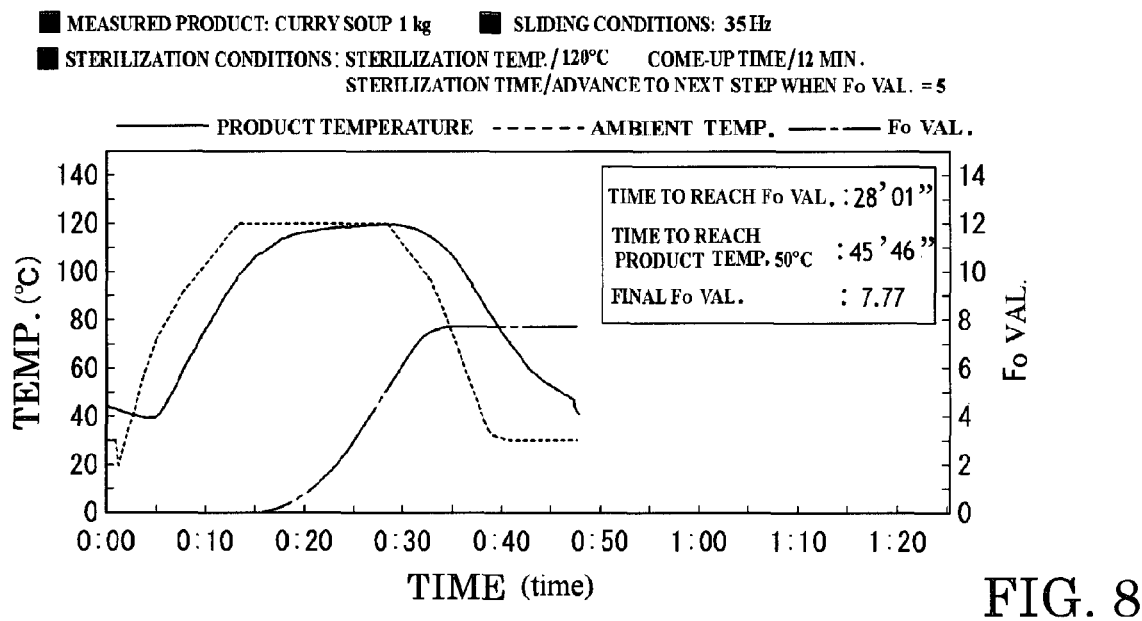
FIG. 8 is a graph showing measurement results in the case of carrying out a sterilization processing test while sliding retorted products at 35 Hz according to the retort sterilizing method of the present invention.

In addition, the graph of FIG. 8 shows the results of carrying out sterilization processing while sliding the retorted products at a sliding frequency of 35 Hz, and in this example, the amount of time from the start of sterilization until the Fo value reaches 5 was 28 minutes 01 second, the amount of time from the start of sterilization until the product temperature has decreased to 50° C. after entering the cooling step following heating was 45 minutes 46 seconds, and the final Fo value was 7.77.

Figure 9:
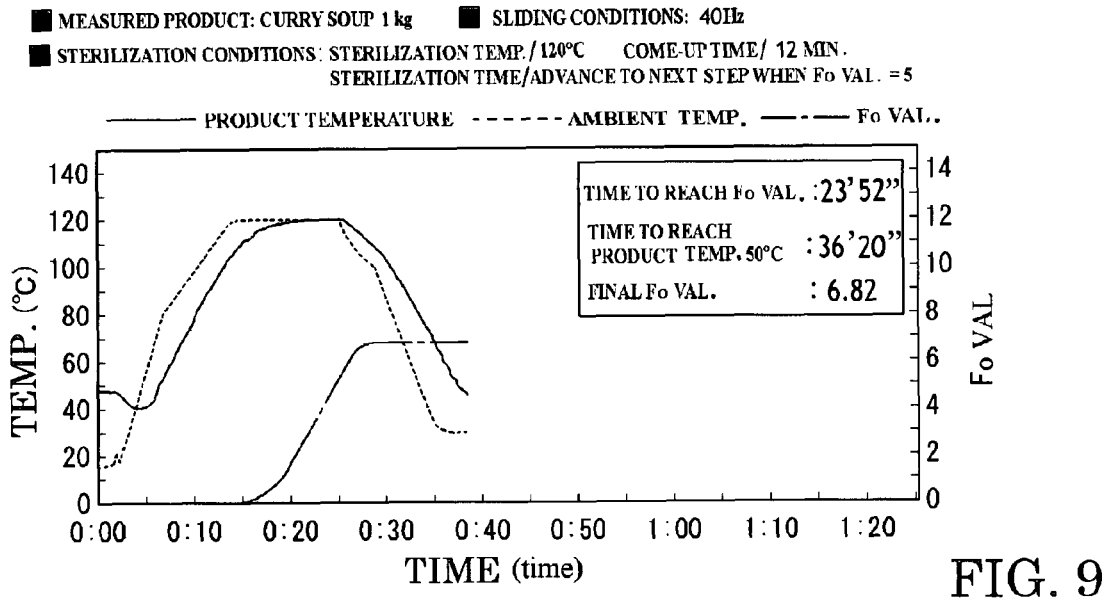
FIG. 9 is a graph showing measurement results in the case of carrying out a sterilization processing test while sliding retorted products at 40 Hz according to the retort sterilizing method of the present invention.

In addition, the graph of FIG. 9 shows the results of carrying out sterilization processing while sliding the retorted products at a sliding frequency of 40 Hz, and in this example, the amount of time from the start of sterilization until the Fo value reaches 5 was 23 minutes 52 seconds, the amount of time from the start of sterilization until the product temperature has decreased to 50° C. after entering the cooling step following heating was 36 minutes 20 seconds, and the final Fo value was 6.82.

Figure 10:
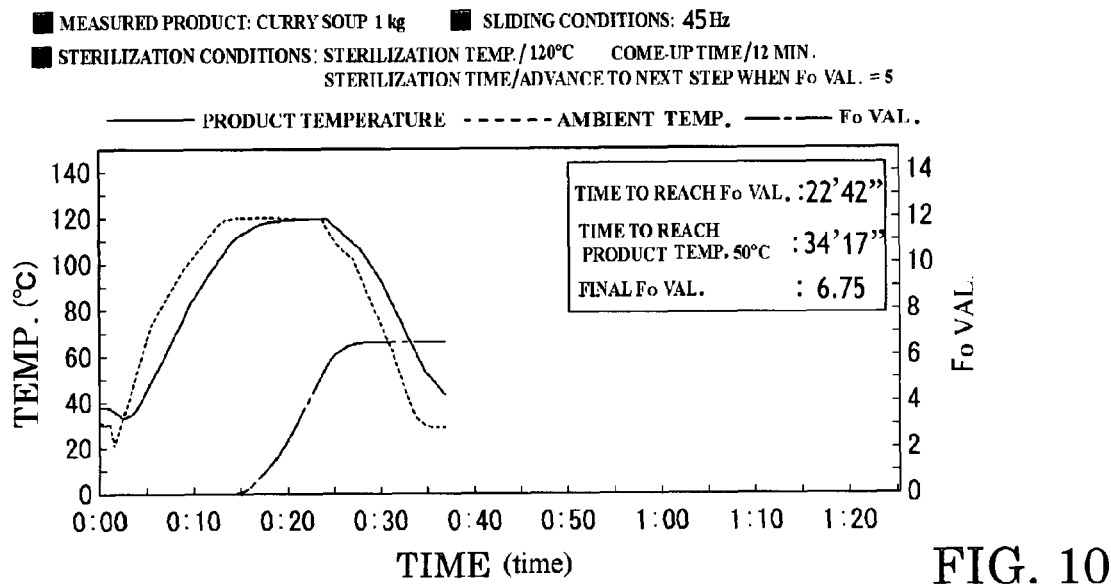
FIG. 10 is a graph showing measurement results in the case of carrying out a sterilization processing test while sliding retorted products at 45 Hz according to the retort sterilizing method of the present invention.

In addition, the graph of FIG. 10 shows the results of carrying out sterilization processing while sliding the retorted products at a sliding frequency of 45 Hz, and in this example, the amount of time from the start of sterilization until the Fo value reaches 5 was 22 minutes 42 seconds, the amount of time from the start of sterilization until the product temperature has decreased to 50° C. after entering the cooling step following heating was 34 minutes 17 seconds, and the final Fo value was 6.75.

In addition, although not shown in the drawings, in the case of carrying out sterilization processing with the retorted products in a stationary state without sliding the carriages to serve as a comparative example, the amount of time from the start of sterilization until the Fo value reaches 5 was 110 minutes, the amount of time from the start of sterilization until the product temperature has decreased to 50° C. after entering the cooling step following heating was 2 hours 45 minutes, and the final Fo value was 7. In addition, in the case, observation of the status of the retorted products following sterilization revealed the presence of portions in which the contents were partially scorched, or in other words, portions in which so-called "retort browning" occurred. On the basis of these results, according to the sterilizing method of the present invention, sterilization time was confirmed to be able to be shortened considerably as compared with conventional methods, and the contents of retorted products were confirmed to be able to be uniformly sterilized without the occurrence of scorched portions or portions that escaped sterilization.

Although the carriages were slid at the same frequency from the start to completion of processing in the above embodiments, the motor serving as a rotating drive source during retort operation can be switched on and off and the speed thereof can be controlled as desired, and the sliding frequency of the carriages during retort processing can be controlled as desired by switching on and off and freely controlling the speed of motor. In the case the contents to be sterilized are susceptible to separation of an oil fraction or susceptible to foaming, there are cases in which it is desirable to not slide the contents as much as possible. In such cases, sterilization can be carried out efficiently and uniformly without having an effect on the contents by holding sliding to the absolute minimum.

Figure 11:
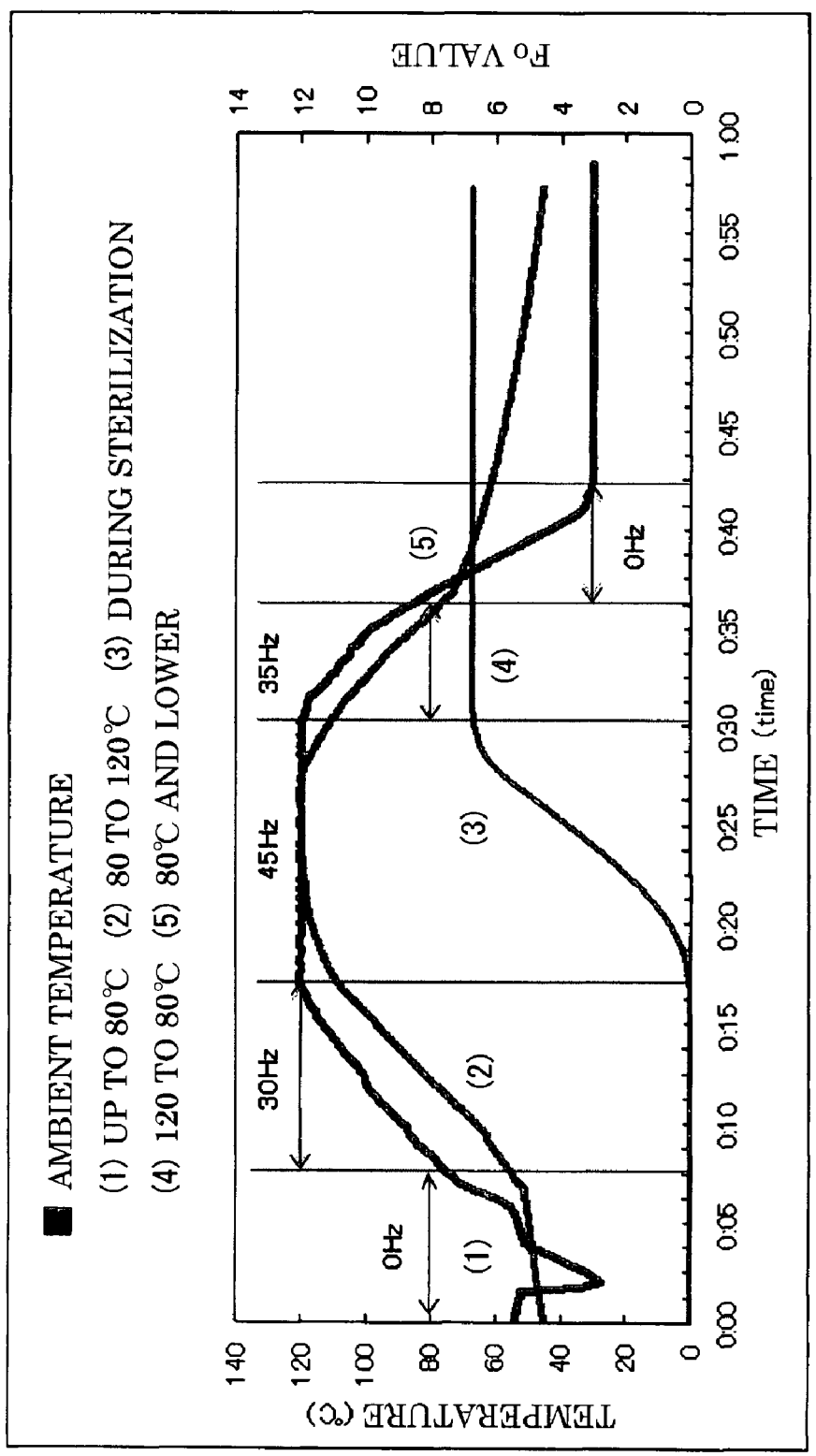
FIG. 11 is a graph showing an example of the case of changing the sliding frequency of carriages during a retorting operation according to the retort sterilizing method of the present invention.
Figure 12:
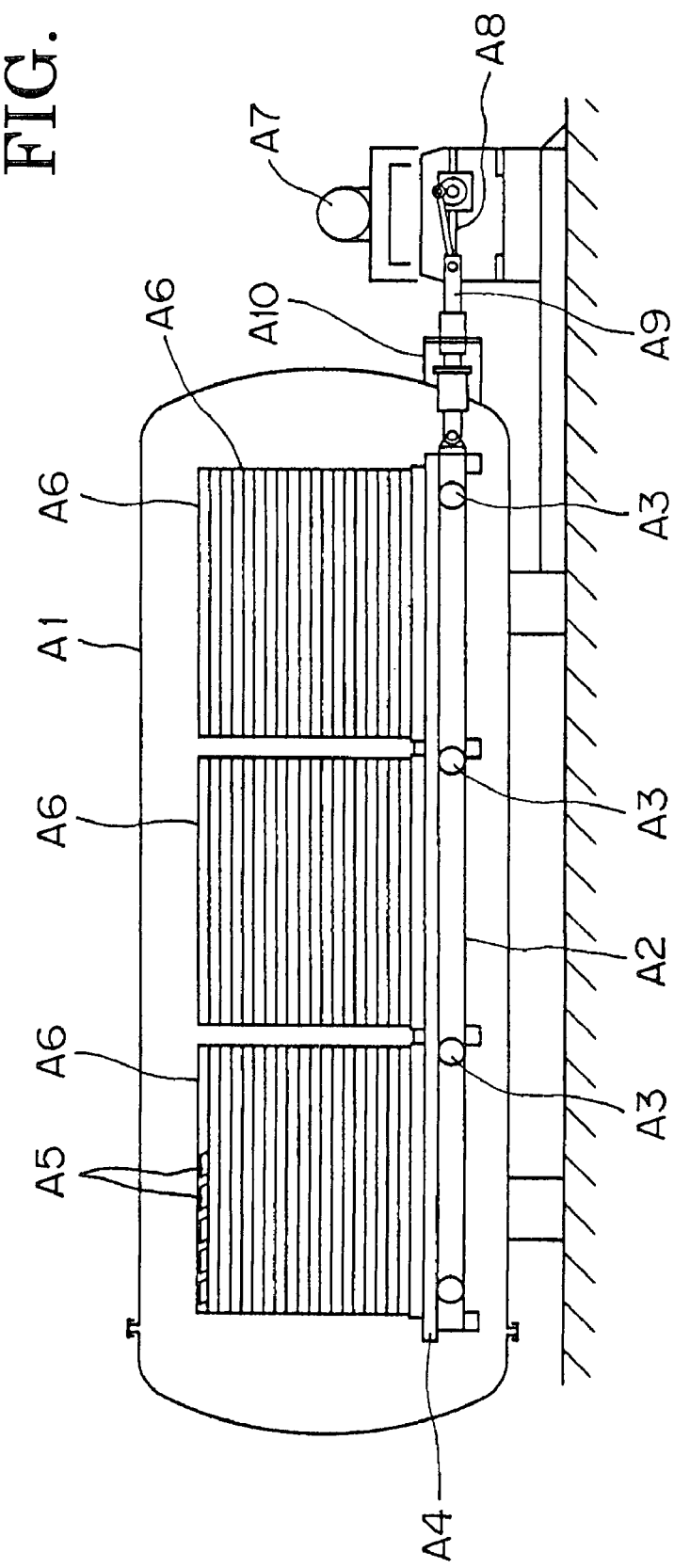
FIG. 12 is a longitudina cross-sectional view of a retort sterilizing apparatus proposed in the prior art.

FIG. 11 shows an example of the case of changing the sliding pattern by controlling the sliding frequency of the carriages during retort operation to the optimum frequency according to the ambient temperature. In this example, the pattern used for sterilization processing consists of not sliding the carriages until the ambient temperature following the start of processing reaches 80° C. (namely, sliding frequency of 0 Hz with the motor switched off), sliding the carriages at 30 Hz until the sterilization temperature rises from 80° C. to the sterilization temperature of 120° C., sliding at 45 Hz during sterilization, lowering the sliding frequency to 35 Hz following completion of sterilization until the temperature falls to 80° C. in the cooling step, and then discontinuing sliding when the ambient temperature has fallen to 80° C. Since product temperature can be controlled by arbitrarily changing the sliding pattern during processing in this manner, retort processing can be carried out under the optimum conditions at all times without causing excessive sliding simply by presetting the pattern in accordance with the type of product to be sterilized by determining the optimum sliding pattern in advance for each type or size of product to be sterilized and then storing that pattern in a controller in the form of a program. In addition, there is also the advantage of extending the service life of the retort apparatus itself by holding sliding of the carriages to the absolute minimum in this manner. Although changing the sliding pattern was carried out according to ambient temperature in the example above, the sliding frequency can also be changed according to product temperature by monitoring product temperatures of products to be sterilized, for example.

INDUSTRIAL APPLICABILITY

The sterilizing method and sterilizing apparatus for retorted products of the present invention can be used to sterilize retorted products having foods or pharmaceuticals and the like sealed inside, and are particularly preferable for retorted products in which solid products or highly viscous contents are sealed in a packaging bag and the like and which use a large or thick packaging bag.

The invention claimed is:

1. A sterilizing method for retorted products, the method comprising steps of: providing one or more carriages, on which retorted products are placed, within a retort; sliding the one or more carriages within the retort while carrying out heat sterilization processing on the retorted products; transmitting driving forces of at least one drive source installed outside to a leftward or rightward side of the retort to the carriages after being converted to reciprocal motion, wherein the sliding occurs reciprocally at a preset prescribed cycle in forward and backward or leftward and rightward directions of the retort, and changing a sliding frequency of the carriages when raising the ambient temperature, sterilizing and lowering the ambient temperature within the retort during the present prescribed cycle of the heat sterilization processing, wherein the carriages are reciprocally slid at a maximum frequency when the ambient temperature has reached a sterilization temperature.

2. The sterilizing method for retorted products according to claim 1, wherein the drive source includes s a rotating drive source using a motor installed outside the retort, rotary motion of the rotating drive source is transmitted to the carriages after being converted to reciprocal motion by a cam mechanism, and the carriages are slid in the forward and backward or leftward and rightward directions of the retort.

3. The sterilizing method for retorted products according to claim 1, wherein the drive source includes a linear reciprocating drive source provided independently for each of the one or more carriages and provided in a direction perpendicular to a lengthwise direction of the retort, and the one or more carriages are slid independently in a horizontal direction perpendicular to the lengthwise direction by the linear reciprocating drive source.

4. The sterilizing method for retorted products according to claim 1 or 2, wherein said one or more carriages includes a plurality of carriages arranged in a row in a lengthwise direction of the retort, and further comprising a step of varying at least one of either a cycle or phase of the sliding one or more between the carriages arranged in a row in the lengthwise direction in the retort.

5. The sterilizing method for retorted products according to claim 4, wherein said plurality of said carriages are supported to reciprocate in a mutually different phase such as to suppress resonance.

6. The sterilizing method for retorted products according to claim 1 or 2, wherein a sliding pattern is changed in accordance with products to be sterilized by controlling the sliding frequency of the one or more carriages during retort processing.

7. The sterilizing method for retorted products according to claim 1, wherein said one or more carriages are provided so as to respectively slide reciprocally in a lengthwise direction or a horizontal direction perpendicular to the lengthwise direction, and hold trays housing the retorted products; and wherein the at least one drive source is installed outside the retort to a leftward or rightward lateral side of the retort.

8. The sterilizing method for retorted products according to claim 7, wherein the at least one drive source includes a rotating drive source using a motor installed outside the retort, a rotating drive shaft driven by the rotating drive source rotatably passes through a retort wall by means of a shaft sealing mechanism, the rotating drive shaft drives a cam mechanism within the retort by being coupled thereto, rotary motion of the rotating drive shaft is transmitted to the one or more carriages after being converted to the reciprocal motion by the cam mechanism, and the one or more carriages are slid in forward and backward or leftward and rightward directions of the retort.

9. The sterilizing method for retorted products according to claim 8, wherein the cam mechanism is constituted by eccentric cams rotated and driven by the rotating drive source, and cam followers attached to the one or more carriages.

10. The sterilizing method for retorted products according to claim 7, wherein the at least one drive source includes a linear reciprocating drive source provided independently for each of the one or more carriages and using a plurality of cylinder apparatuses provided in a direction perpendicular to the lengthwise direction of the retort.

11. The sterilizing method for retorted products according to claim 7, wherein the one or more carriages include a plurality of carriages arranged in a row in a lengthwise direction of the retort, and the at least one drive source drives the plurality of carriages by varying at least one of either a cycle or phase of the sliding between the plurality of carriages arranged in a row in the lengthwise direction in the retort.

12. sterilizing method for retorted products according to claim 7, wherein a speed of the at least one drive source is variable, and a sliding pattern can be changed in accordance with products to be sterilized by controlling the sliding frequency of the one or more carriages during retort processing.

13. The sterilizing method for retorted products according to claim 1, wherein the at least one drive source includes a rotating drive source using a motor installed outside the retort which imparts rotational force to a rotary shaft that penetrates through a lateral side of the retort, and wherein rotary motion of the rotary shaft is converted to the reciprocal motion inside said retort.

14. The sterilizing method for retorted products according to claim 1, wherein the at least one drive source includes at least one linear reciprocating drive source provided substantially perpendicular to a lengthwise direction of the retort and installed outside the retort which imparts a reciprocating force to a shaft that penetrates through a lateral side of the retort.

15. The sterilizing method for retorted products according to claim 1, wherein the retort includes a first cover located at an upstream location of said retort into which products to be retorted are inserted and a second cover located at a downstream location in a lengthwise direction of the retort from which the retorted products are removed, and wherein said at least one drive source is located at a lateral side of said retort allowing unobstructed access to said first and second covers.

16. A sterilizing method for retorted products, the method comprising steps of: providing a plurality of carriages, on which retorted products are placed, within a retort; sliding said plurality of carriages within the retort while carrying out heat sterilization processing on the retorted products;

transmitting a driving force of a drive source installed outside the retort to the plurality of carriages after being converted to reciprocal motion; wherein the sliding occurs reciprocally at a preset prescribed cycle in forward and backward or leftward and rightward directions of the retort; and varying at least one of either a cycle or phase of the sliding between the plurality of carriages arranged in a row in a lengthwise direction in the retort.

\* \* \* \* \*